Figure 1:
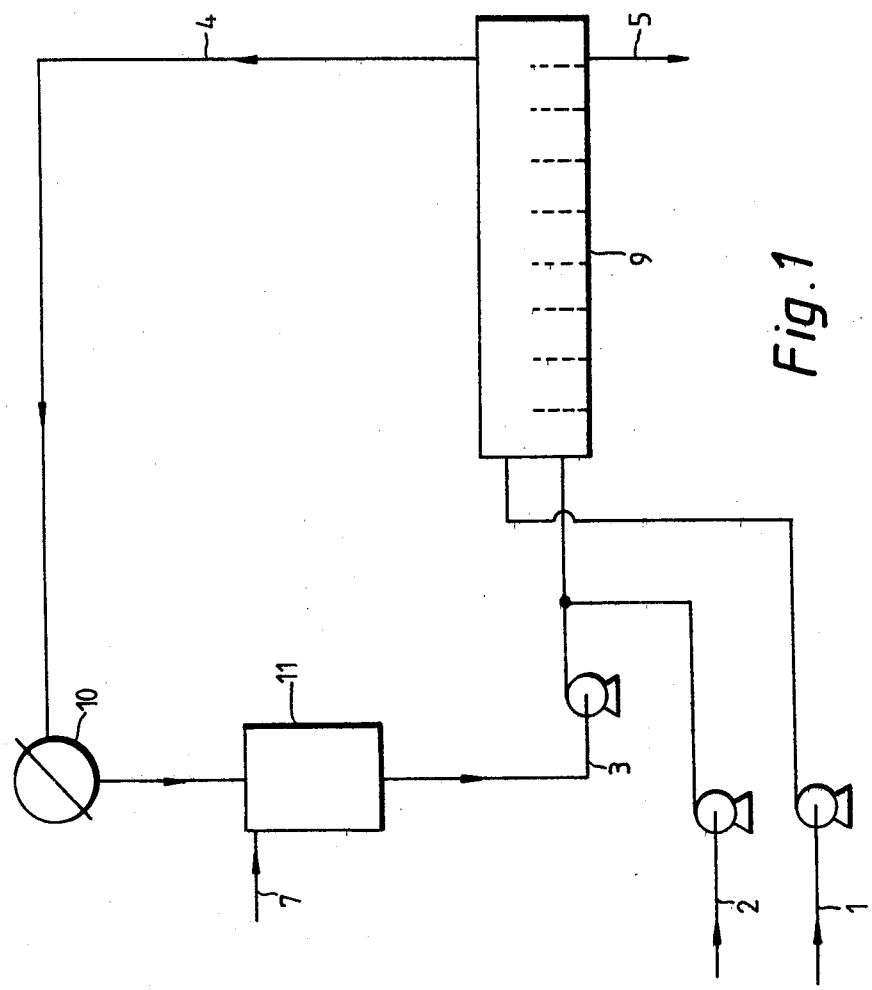

United States Patent [19]

Langley

[11] 4,310,712

[45] Jan. 12, 1982

[54] PROCESS FOR THE PRODUCTION OF PHENOL AND ACETONE

[75] Inventor: Phillip E. Langley, Middlesbrough, England

[73] Assignee: Imperial Chemical Industries Limited, London, England

[21] Appl. No.: 140,600

[22] Filed: Apr. 15, 1980

[30] Foreign Application Priority Data

Apr. 20, 1979 [GB] United Kingdom ............... 13904/79
Jul. 4, 1979 [GB] United Kingdom ............... 23269/79

[51] Int. Cl.³ ............................................. C07C 37/08
[52] U.S. Cl. .................................... 568/798; 568/768
[58] Field of Search ....................... 568/798, 768, 741

[56] References Cited

U.S. PATENT DOCUMENTS 2,663,735 12/1953 Filar et al. ........................... 568/798
3,187,052 6/1965 Nelson et al. ....................... 568/798
3,215,745 11/1965 Frank ................................... 568/798
4,006,194 2/1977 Luberoff et al. ..................... 568/798

FOREIGN PATENT DOCUMENTS 30331 4/1971 Australia .
1598110 10/1970 France .
910301 11/1962 United Kingdom .
1313360 4/1973 United Kingdom .
1342835 1/1974 United Kingdom .
462812 8/1975 U.S.S.R. ............................. 568/798

Primary Examiner—Werren B. Lone
Attorney, Agent, or Firm—Cushman, Darby & Cushman

[57] ABSTRACT

Cumene hydroperoxide is decomposed to phenol and acetone by mixing it with acetone and a catalyst, flowing it without substantial back mixing through a reactor and controlling the reaction temperature by evaporating acetone and thus reducing the acetone concentration of the mixture in the course of the reaction.

10 Claims, 3 Drawing Figures

PROCESS FOR THE PRODUCTION OF PHENOL AND ACETONE

This invention relates to the production of phenol and acetone.

Phenol and acetone may be produced by the decomposition of cumene hydroperoxide. Cumene hydroperoxide is normally produced from cumene by oxidation with oxygen and usually contains unconverted cumene and phenyl dimethyl carbinol byproduct even after an optional concentration step. Decomposition is usually carried out in the presence of a catalyst, for example an acid catalyst especially sulphuric acid. The decomposition of cumene hydroperoxide to phenol and acetone is the most commercially important process for producing phenol.

It is known that the above process gives rise to a number of byproducts especially alpha methyl styrene ansd derivatives thereof particularly dimers of alpha methyl styrene, cumyl phenol and tarry polymeric materials.

In British Pat. No. 1,313,360 it is disclosed that when the decomposition of an aralkyl hydroperoxide to a phenol and a carbonyl compound is carried out under conditions in which substantially complete back mixing of the reaction products with reactants takes place and especially if the residence times in the reactor are high the level of cleavage reaction side products is increased. A process is described in the patent involving carrying out the reaction with little back mixing (i.e. at a low hold back value) under a pressure such that no substantial vaporisation within the reaction chamber occurs. A main objective of that invention was to reduce the discolouration of the phenol produced by highly coloured byproducts.

USSR Pat. No. 851 851 discloses flowing decomposing cumene hydroperoxide through a multi section reactor and adding cold acetone to each section to stabilise the temperature.

According to the present invention a process of the above type is provided whereby the production of alpha methyl styrene relative to its derivatives may be enhanced. Alpha methyl styrene may be removed as a valuable by-product useful for example in the manufacture of resins or may be hydrogenated to cumene which may be reused in the process after oxidation to cumene hydroperoxide, whereas its derivatives must be cracked to regenerate alpha methyl styrene. In general such cracking regenerates only part of the alpha methyl styrene. One of the derivatives, cumyl phenol, is believed to be formed by reaction between alpha methyl styrene and phenol and this also reduces the yield of the phenol in the process.

The decomposition of cumene hydroperoxide to phenol and acetone is strongly exothermic, which presents problems of temperature control. It is a feature of this invention that the temperature during the reaction is controlled by permitting acetone to evaporate from the reaction medium.

According to the invention a process of producing phenol, acetone and alpha methyl styrene from cumene hydroperoxide comprises mixing acetone and a decomposition catalyst which may be an acidic catalyst, for example sulphuric acid, with cumene hydroperoxide, the acetone being preferably in an amount in the range 5 to 12 and more preferably 8 to 10 moles per mole of cumene hydroperoxide, flowing the mixture without substantial back mixing at a reaction temperature until conversion of the cumene hydroperoxide to phenol and acetone is substantially complete and controlling the temperature at least in part by evaporating acetone from the mixture and thereby reducing the acetone concentration of the mixture in the course of the reaction. Phenol, acetone and alpha methyl styrene may be recovered from the product.

The reaction temperature may be for example 60° to 120° C. and is preferably 80° to 110° C. The concentration of sulphuric acid when this is used as the catalyst is suitably in the range 0.01 to 0.3% and is preferably 0.03 to 0.1% by weight of the cumene hydroperoxide fed. The reaction is suitably carried out at a residence time of 1 to 30 minutes and preferably 3 to 10 minutes. The pressure is suitably 0.25 to 2 for example 0.5 to 1.0 bars absolute.

The acetone which is added to the cumene hydroperoxide may be derived wholly from that which is evaporated in the course of the reaction or may be supplemented if desired for example by acetone recovered in later stages of the process.

The cumene hydroperoxide may be supplied as a solution in an unreactive diluent, for example cumene, if desired, for example in a concentration of 50 to 90% by weight of cumene hydroperoxide based on the total of cumene hydroperoxide and cumene fed.

The phenol, acetone and alpha methyl styrene may be recovered from the product in known manner, for example by distillation.

The invention is also attractive in that the acetone vapour removed from the reaction is a valuable source of heat which can be used in the purification of acetone in the process. This heat may suitably be utilised by distilling the reaction product to separate a crude acetone stream, and passing this stream to an intermediate point of a distillation column from which purified acetone is removed as a top product and to the base of which is fed acetone vapour removed from the reactor. By this means the heat required for this distillation is at least in part supplied by the acetone vapour removed from the reactor. This distillation may otherwise be carried out conventionally according to the desired purity of distilled acetone which is required. Acetone withdrawn from the base of the column is returned to the reactor.

The reaction may be carried out according to this invention in apparatus which is simple and reliable because of its freedom from mechanical moving parts, as described below.

The apparatus may comprise a conduit through which the reaction mixture is flowed, the conduit being divided by at least 2 plates disposed across the conduit as a restriction to flow of the liquid, the conduit having a vapour space above the liquid in each of the compartments formed. Such conduits may permit the liquid to flow through perforations in them or may serve as weirs, thus preventing any substantial back mixing from material beyond them. It has been found that a substantially horizontal conduit in which dividing plates are perforated is very effective especially if the perforations are evenly disposed over the whole of the liquid-contacting area of the plate because as well as avoiding back mixing between the compartments into which the conduit is divided they minimise the presence of dead areas in which localised pockets of reactants are subject to longer hold-up time. It is desirable that sufficient perforations of suitable size should be provided to prevent the formation of high velocity jets of liquid passing directly through the compartments but the perforations should not account for a sufficiently high proportion of the surface area of the plate to allow appreciable back mixing.

Suitably 3 to 50 for example 5 to 20 such perforated plates are provided along the length of the conduit and the ratio of the length of each compartment into which the conduit is divided to the width of the conduit is suitably 1:2 to 2:1.

The conduit may be a tube. To permit evaporation of the acetone the conduit should not be completely filled; for example it may be filled to the extent of 10 to 80% by volume. Acetone vapour may be withdrawn from the conduit at one or several points as desired.

This construction of a reactor is attractive in that it is unnecessary to provide stirrers in the reactor, thus avoiding the use of moving parts in an environment of reactants and because the temperature of the reaction may readily be controlled by the rate of acetone feed and by the pressure in the reactor. The system is attractive in terms of its safety and efficiency of heat removal. It permits effective removal of the heat of reaction at low residence times.

One form of the invention will now be described with reference to the accompanying drawings, FIG. 1 shows a flow sheet of apparatus for carrying out the invention.

Line 1 leads via a pump to reactor 9 and lines 2 and 3 lead via pumps to a common inlet line to reactor 9. Reactor 9 is a horizontal tube divided into 9 compartments of substantially equal volume by baffles and having a capacity of 60 ml of liquid, the space above the liquid being available for vapour. Line 5 draws liquid from the last compartment and line 4 removes vapour from the vapour space to a condenser 10 which feeds a receiver 11 to which an auxillary feedline 7 is provided.

Figure 2:
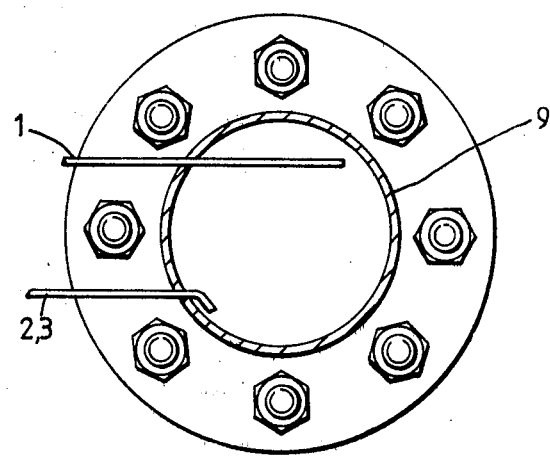
Figure 3:
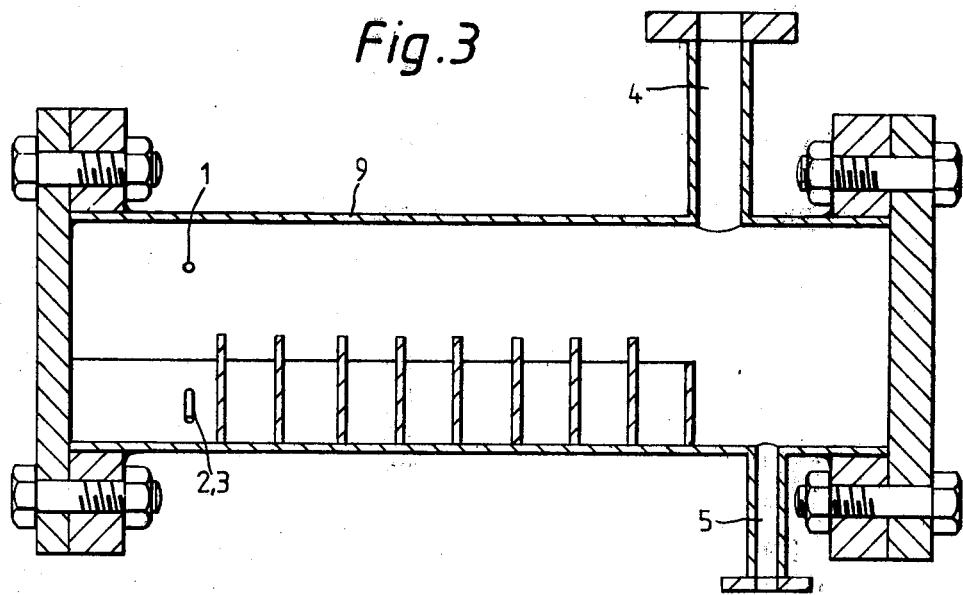

FIG. 2 and FIG. 3 shows respectively a transverse and longitudinal cross-section through reactor 9. Each of the first eight baffles is pierced by 60 to 65 perforations which are evenly distributed across the baffle, the perforations of each baffle being out of line with those on the baffles on either side of it.

EXAMPLE 1

A cumene oxidate (300 g/hr) comprising 75% by weight cumene hydroperoxide, 7% by weight of phenyl dimethyl carbinol and 21% by weight cumene, was fed via line 1 to reaction vessel 9. 0.15 g/hr of concentrated sulphuric acid was fed through line 2 and 450 g/hr of recycled condensate from the reactor of composition 95% by weight acetone together with cumene and water was fed through line 3. Nothing was fed through line 7. The reaction vessel was maintained at atmospheric pressure and at an average temperature of 95° C. Vapor evolved was withdrawn via line 4, condensed at a rate of 540 g/hr and returned as the recycled distillate. The reaction product collected over 1 hour contained approximately 137.8 g of phenol, 85.9 g of acetone, 12.8 g of alpha methyl styrene and 2.9 g of cumyl phenol.

EXAMPLE 2

300 g/hr of a cumene oxidate comprising 75% by weight of cumene hydroperoxide, 7% by weight of phenyl dimethyl carbinol and 21% by weight cumene, was fed via line 1 to reaction vessel 9. 0.19 g/hr of concentrated sulphuric acid was fed through line 2 and 540 g/hr of recycled distillate recovered from the reactor vapour together with 86 g/hr of fresh acetone (fed via line 7) was fed through line 3. The reaction vessel was maintained at atmospheric pressure and at an average temperature of 85° C. Vapour was recovered via line 4, condensed in condenser 10 and recycled. The reaction product collected over 1 hour contained approximately 138.7 g of phenol, 171.9 g acetone, 15.1 g alpha methyl styrene and 1.0 g of cumyl phenol.

It is claimed:

1. In a process of producing phenol, acetone and alpha methyl styrene from cumene hydroperoxide which comprises mixing acetone and a decomposition catalyst with cumene hydroperoxide, flowing the mixture without substantial back mixing at a reaction temperature until conversion of the cumene hydroperoxide to phenol and acetone is substantially complete,
   the improvement comprising controlling the temperature of the reaction at least in part by evaporating acetone from the mixture and thereby reducing the acetone concentration of the mixture in the course of the reaction.

2. A process as claimed in claim 1 in which the decomposition catalyst is sulphuric acid.

3. A process as claimed in claim 1, in which the temperature is 80° to 110° C.

4. A process of producing phenol, acetone and alpha methyl styrene from cumene hydroperoxide which comprises:
   (1) mixing acetone and sulfuric acid as a decomposition catalyst with cumene hydroperoxide,
   (2) flowing the mixture for a residence time of 1 to 30 minutes and without substantial back mixing at a reaction temperature of 60° C. to 120° C. until conversion of the cumene hydroperoxide to phenol and acetone is substantially complete, and
   (3) controlling the temperature of the reaction at least in part by evaporating acetone from the mixture and thereby reducing the acetone concentration of the mixture in the course of the reaction.

5. A process as claimed in claim 4 in which 5 to 12 moles of acetone are mixed with each mole of cumene hydroperoxide.

6. A process as claimed in claim 4 which is carried out at a pressure of 0.5 to 1 bar absolute.

7. A process as claimed in claim 4 in which the cumene hydroperoxide is supplied in a solution in cumene which solution comprises 50 to 90% by weight of cumene hydroperoxide based on the total of cumene hydroperoxide and cumene fed.

8. A process as claimed in claim 4 in which acetone vapour removed from the reaction is fed to the base of a distillation column, a crude acetone stream is separated from the reaction product and the crude acetone stream is passed to an intermediate point of the said distillation column and purified acetone is removed as a top product from the said distillation column.

9. A process as claimed in claim 4 in which the reaction mixture is flowed through a conduit which is divided by at least 2 plates disposed across the conduit as a restriction to flow of the liquid, the conduit having a vapour space above the liquid in each of the compartments so formed.

10. The process as claimed in claim 4, wherein the temperature is in the range of 80° C. to 110° C.

* * * * *